US009466220B2

(12) United States Patent
Alekseev et al.

(10) Patent No.: US 9,466,220 B2
(45) Date of Patent: Oct. 11, 2016

(54) METHOD AND ON-BOARD SYSTEM FOR ENSURING THE MINIMUM LONGITUDINAL SEPARATION DISTANCE UNDER WAKE TURBULENT CONDITIONS

(75) Inventors: Sergey Viktorovich Alekseev, Moscow (RU); Nikolay Alekseevich Baranov, Moscow (RU); Andrei Sergeevich Belotserkovskiy, Moscow (RU); Mikhail Igorevich Kanevskiy, Moscow (RU)

(73) Assignees: FSBI (<<FALPIAR>>), Moscow (RU); SERGEY VIKTOROVICH ALEKSEEV, Moscow (RU); NIKOLAY ALEKSEEVICH BARANOV, Moscow (RU); ANDREI SERGEEVICH BELOTSERKOVSKIY, Moscow (RU); MIKHAIL IGOREVICH KANEVSKIY, Moscow (RU)

( * ) Notice: Subject to any disclaimer, the term of this patent is extended or adjusted under 35 U.S.C. 154(b) by 0 days.

(21) Appl. No.: 14/421,586
(22) PCT Filed: Aug. 30, 2012
(86) PCT No.: PCT/RU2012/000717
§ 371 (c)(1),
(2), (4) Date: Feb. 16, 2015
(87) PCT Pub. No.: WO2014/035282
PCT Pub. Date: Mar. 6, 2014

(65) Prior Publication Data
US 2015/0235559 A1 Aug. 20, 2015

(30) Foreign Application Priority Data
Aug. 30, 2012 (RU) ................. 2012136930

(51) Int. Cl.
*G08G 5/00* (2006.01)
*G08G 5/06* (2006.01)
(52) U.S. Cl.
CPC .......... *G08G 5/0095* (2013.01); *G08G 5/0021* (2013.01); *G08G 5/0043* (2013.01); *G08G 5/06* (2013.01)

(58) Field of Classification Search
CPC combination set(s) only.
See application file for complete search history.

(56) References Cited

U.S. PATENT DOCUMENTS 4,735,503 A * 4/1988 Werner .................. G01S 17/95
356/28.5
5,262,773 A * 11/1993 Gordon .................. G01S 7/062
340/949

(Continued)

FOREIGN PATENT DOCUMENTS

| DE | 10039109 A1 | 2/2002 |
| WO | 2005/010554 A1 | 2/2005 |
| WO | 20061083361 A2 | 8/2006 |

OTHER PUBLICATIONS

Search Report issued in International Application No. PCT/RU2012/000717 dated Jun. 6, 2013.

*Primary Examiner* — Jonathan L Sample
(74) *Attorney, Agent, or Firm* — Nath, Goldberg & Meyer; Jerald L. Meyer; Stanley N. Protigal

(57) ABSTRACT

Standardized distance minima for longitudinal separation is ensured during flight of a second aircraft behind a first aircraft on take-off or landing of the aircraft on one runway or on two parallel runways located near to each other, or during flight one behind the other at near altitude levels in conditions where there is the risk of turbulence from the vortex wake of the first aircraft possibly being present along the direction of movement of the second aircraft. Continuous monitoring of the level of wake vortex flight safety of the second aircraft is carried out in a buffer zone which surrounds the aircraft and is selected on the basis of the direction of the aircraft outside the standardized distance minimum, taking into account pilot reaction time and the time for the system for controlling the second aircraft to respond to a command to change speed.

12 Claims, 2 Drawing Sheets

(56) References Cited

U.S. PATENT DOCUMENTS

Figure 1:
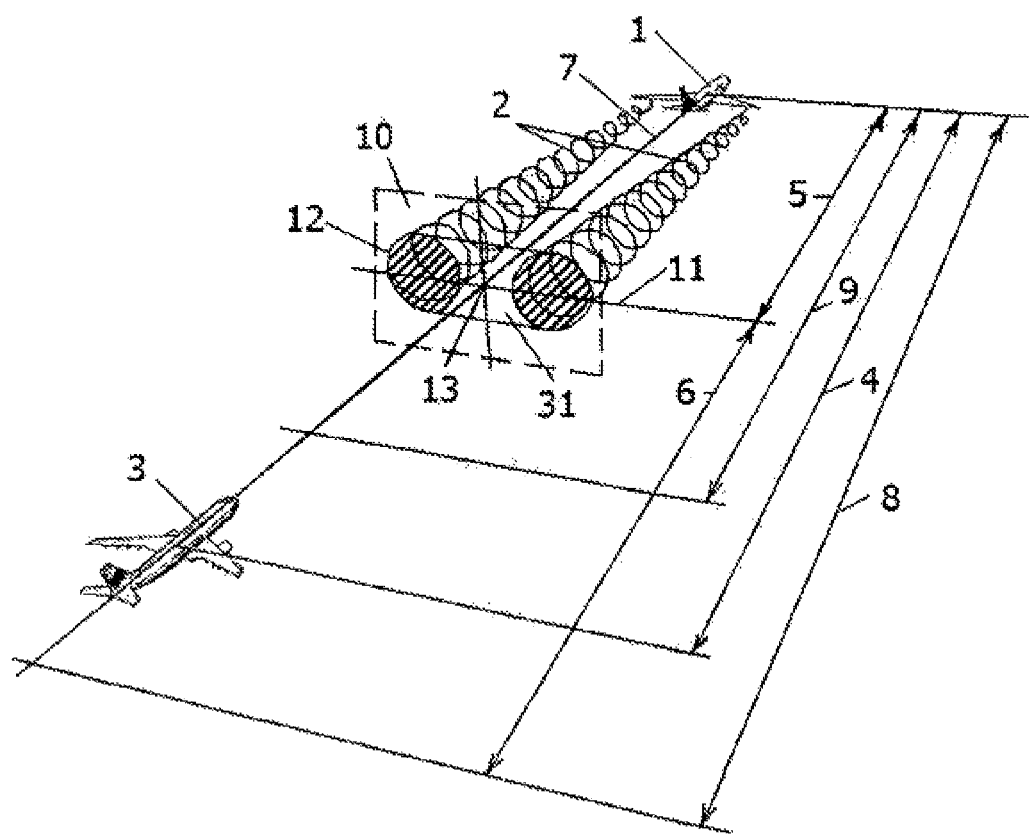

| | | | | |
|---|---|---|---|---|
| 5,596,332 | A * | 1/1997 | Coles | G01S 5/0009 342/455 |
| 6,133,867 | A * | 10/2000 | Eberwine | G01S 5/0072 342/125 |
| 7,385,527 | B1 * | 6/2008 | Clavier | G08G 5/0013 340/945 |
| 2002/0042673 | A1 * | 4/2002 | Ooga | G01S 7/04 701/120 |
| 2002/0075171 | A1 * | 6/2002 | Kuntman | G01C 23/00 340/961 |
| 2002/0089432 | A1 * | 7/2002 | Staggs | G01C 23/00 340/945 |
| 2003/0222795 | A1 * | 12/2003 | Holforty | G01C 23/005 340/968 |
| 2004/0107027 | A1 * | 6/2004 | Boudrieau | B64D 45/0015 701/1 |
| 2004/0182966 | A1 * | 9/2004 | Schneider | G08G 5/0052 244/13 |
| 2006/0216674 | A1 * | 9/2006 | Baranov | G09B 9/08 434/29 |
| 2006/0244637 | A1 * | 11/2006 | Baranov | G01S 13/9303 340/968 |
| 2007/0103340 | A1 * | 5/2007 | Baranov | G01C 23/00 340/968 |
| 2008/0030375 | A1 * | 2/2008 | Cotton | G01S 17/023 340/945 |
| 2010/0001882 | A1 * | 1/2010 | Jeddi | G05D 1/0676 340/961 |
| 2010/0017127 | A1 * | 1/2010 | Pepitone | G08G 5/0078 701/301 |
| 2010/0217510 | A1 * | 8/2010 | Deker | G08G 5/045 701/120 |
| 2010/0283635 | A1 * | 11/2010 | Brinkman | G01C 23/00 340/961 |
| 2010/0286848 | A1 * | 11/2010 | Stassen | G08G 5/0008 701/3 |
| 2010/0294890 | A1 * | 11/2010 | Journade | B64C 9/12 244/199.1 |
| 2011/0004398 | A1 * | 1/2011 | Stayton | G08G 5/0013 701/120 |
| 2011/0134412 | A1 * | 6/2011 | Inokuchi | G01S 17/58 356/28.5 |
| 2015/0235559 | A1 * | 8/2015 | Alekseev | G08G 5/0095 701/120 |

* cited by examiner

METHOD AND ON-BOARD SYSTEM FOR ENSURING THE MINIMUM LONGITUDINAL SEPARATION DISTANCE UNDER WAKE TURBULENT CONDITIONS

FIELD OF INVENTION

The invention relates to the safety systems of aircraft operation, more particularly, to the methods for ensuring pilot's compliance with the minimum distance between aircraft, set in relation to the conditions of safe separation in the predicted wake turbulence areas for aircraft moving close to the airport terminals, during takeoff and landing.

PRIOR ART

With the continuous growth of air traffic, the problem of flight safety associated with aircraft wake vortices is becoming increasingly important around the world, especially for the aircraft flight conditions near airports during take-off and landing.

Aircraft's encounter with wake vortices can lead to such phenomena as buffeting (frequency-resonant excitation of the aircraft's structural elements), uncontrolled angular velocity rotation about the roll axis (up to 200 degrees per second) with the loss of altitude (up to 150-200 m), as well as to the loss of aircraft control. In this context, the International Civil Aviation Organization (ICAO) developed and introduced the rules defining the longitudinal separation between the first and the second aircraft that ensured safe entry of the second aircraft into the wake vortices generated by the first aircraft, taking into account the design characteristics of both aircraft and atmospheric conditions within the flight area. Later, these rules were subject to the iterated offset intended to increase the minimum distance. This has led to the fact that the major international airports are working at the breaking point of their capacity. However, separation standards for aircraft in terms of wake vortex safety are obligatory during in-trail takeoff or landing operations on the same runway or on two closely spaced parallel runways, or during in-trail flight at neighboring altitudes.

Development of methods and systems which would reduce the distance between aircraft and thereby increase airport handling capacity and aircraft separation density without jeopardizing flight safety, is a very important task.

However, increasing the handling capacity by reducing the standards of intervals between the aircraft, i.e. increasing the flying intensity, leads to a decreased wake vortex safety during takeoff and landing operations.

Well-known is the WakeVortex Advisory System (U.S. Pat. No. 4,137,764, B1), in which the separation distance between the aircraft near runways is minimized by identifying the severity of the existing wind conditions at a pre-selected path point and forecasting the wake turbulence movement, in particular, its moving away from the flight path under determined weather conditions. However, the use of this system implies a possibility of reducing the minimum distance between aircraft depending on the actual weather conditions in each of the real-life situations, which is unacceptable for flight planning and traffic control in terms of obligatory compliance with established separation standards.

It is known that entering a wake vortex or turbulence hazard area—can be avoided through maneuvering with a consistent change in current aircraft speed, e.g. by a change in engine thrust or power.

For example, a passenger aircraft navigation device is known (JP, 2000062698, A1) that is intended for turbulence avoidance by evaluating the detected turbulence, flight routing and fast change of the aircraft flightpath to exit the turbulence area. Moreover, when the turbulence area is detected and analyzed by the flight management system, the cockpit receives an alarm signal, and simultaneously a device for automatic adjustment of engine power turns on. An automatic steering control device is continuously operated to avoid entering into such an air space by starting the flight management system for the required minimal change of the flight route.

A method for safely managing aircraft separation (U.S. 2008030375, A1) is known, in which, based on the information about the leading and following aircraft and weather data; the future wake positions of the leading aircraft are predicted. One can determine whether the future trajectory of the following aircraft will cross the predicted area of the wake vortices generated by the leading aircraft, and alert the ATC service to the possible point of intersection. Then the correction of the following aircraft flight is determined, compatible with the traffic, to avoid the point of intersection with wake vortices, and the correction is transmitted to the ATC. However, the decision-making system is not quick-operating; the decision to change the course is taken by the flight operations officer, who informs the pilot of the following aircraft about the corrected subsequent flight parameters.

However, the above-described navigation device (JP, 2000062698, A1) and safely managing aircraft separation method (U.S., 2008030375, A1) cannot be used for tense flight complying with the specified minimum separation distances, as maneuvering with a temporary change of course and the subsequent return to the original predetermined course requires considerable space, time and fuel and can lead to undesirable significant increase in the distance between the aircraft and to the airport capacity reduction.

Furthermore, the authors note that the abovementioned methods provide the pilot with the visualization of not real, but predicted situations that require the pilot's logic conclusions in order not to enter the area of forecasted danger by making changes in flight parameters, performing an evasive maneuver to change the course and/or position of the aircraft in space within the limits agreed with the ATC officer. This leads to the risk of "human factor", significantly impacting the flight operation, as being conditioned by the experience of the pilot and ATC officer and their ability of making quick decisions, while not ensuring compliance with the separation requirements and required level of safety when resolving real time conflict situations.

DISCLOSURE OF THE INVENTION

The aim of the present invention is to provide a method for monitoring and correction of separation distances during in-trail flight, providing an increase in airport capacity without compromising wake vortex safety, in full compliance with the established standardized longitudinal separation distances.

When creating the present invention, the authors were tasked to develop a method and on-board system for ensuring standardized minimum longitudinal separation distance for in-trail flight during takeoff or landing on the same runway or on two parallel runways located near each other, or during in-trail flight at neighbouring altitudes when there is a risk of possible wake turbulence from the first aircraft along the course of the second aircraft. This is achieved through continuous wake vortex flight safety monitoring and velocity control for the second aircraft in a situation of decreasing wake vortex safety, to ensure the distance between the aircraft that exceeds the standardized minimum longitudinal separation distance by the permissible value defined with regard to the ability of the second aircraft to change its velocity at the command for deceleration or acceleration.

The task was solved by developing a method for ensuring minimum longitudinal separation distance under wake turbulence conditions with at least one leading aircraft, generating wake vortices and the second aircraft following the first one, during takeoff or landing of said aircraft on the same runway or on two parallel runways located near each other, or during in-trail flight at neighboring altitudes when there is a risk of possible wake turbulence from the first aircraft along the course of the second aircraft, in which:

value of the buffer zone, which ensures the responsiveness of the pilot and the control system of the second aircraft to the command for changing its flight velocity, is selected;

value of the recommended maximum distance between the first and the second aircraft is determined as the sum of values of the standardized minimum separation distance for the interaction of the first and the second aircraft under wake turbulence conditions, and the buffer zone value. At the same time, the maximum recommended distance is defined as the distance along the sight line connecting the gravity centers of the first and the second aircraft;

value of the reference distance is determined as the arithmetic average between the values of the specified standardized minimum separation distance and the recommended maximum distance, to monitor the current actual deviation from this recommended maximum distance;

value of the current actual distance between the first and the second aircraft is continuously determined and compared with the values of the recommended maximum distance, the reference distance and the minimum separation distance, to detect the exceedance, equality or reduction of the actual distance value in comparison with the specified values;

air space along the course of the second aircraft in a simulated reference plane on the edge of the buffer zone with the standardized minimum separation distance is continuously monitored, and the presence or absence of wake turbulence in the specified reference plane and its danger for the second aircraft is reported;

when detecting wake turbulence in the reference plane, endangering the second aircraft, the risk of interaction of the second aircraft with the specified turbulence is estimated, and, if the obtained risk assessment exceeds the acceptable risk thresholds, the location of the specified turbulence is defined as inadmissible for entering by the second aircraft;

a deceleration command is generated in case of detection of an inadmissible area on the edge of the buffer zone and if the actual distance is less than the value of the reference distance;

a deceleration command is generated when no inadmissible area is present on the edge of the buffer zone and if the actual distance is less than the value of the reference distance, a deceleration command is generated when no inadmissible area is present on the edge of the buffer zone and if the actual distance is equal to the standardized minimum separation distance;

an acceleration command is generated when no inadmissible area is present on the edge of the buffer zone and if the actual distance is larger than the maximum reference distance;

an acceleration command is generated when no inadmissible area is present on the edge of the buffer zone and if the actual distance is larger than the recommended maximum distance;

the following information is saved and transmitted to the traffic control unit in the dynamic mode:

mutual position of the second and the first aircraft along the course of the second aircraft;

value of the selected buffer zone;

value of the calculated recommended maximum distance;

value of the calculated reference distance;

value of the actual distance between the first and the second aircraft;

information on the necessity of transition to the deceleration mode, on the receipt of the deceleration command by the control system of the second aircraft, on the movement of the second aircraft in the deceleration mode, on the termination of the deceleration mode;

information on the necessity of transition to the acceleration mode, on the receipt of the acceleration command by the control system of the second aircraft, on the movement of the second aircraft in the acceleration mode, on the termination of the acceleration mode;

the screen of the second aircraft displays in the dynamic mode information at least on the value of the actual distance between the first and the second aircraft and, with the help of at least light indication, information on the necessity of transition to the deceleration mode, on the deceleration command receipt, on the execution of the deceleration mode, on the termination of the deceleration mode; information on the necessity of transition to the acceleration mode, on the receiving the acceleration command by the control system of the second aircraft, on the execution of the acceleration mode, on the termination of the acceleration mode;

during the respective light indication, the pilot of the second aircraft is provided with a possibility to execute the deceleration mode or the acceleration mode using standard techniques of deceleration or acceleration, or to maintain the current mode without changes.

Furthermore, according to the invention, it is expedient to perform the light indication of deceleration, acceleration and constant velocity modes by activating indicators of different colors.

Furthermore, according to the invention, it is expedient to display the expedient or acceleration command receipt by an intermittent light indication.

Furthermore, according to the invention, it is expedient to determine the standardized minimum longitudinal separation distance for wake turbulence by taking into account the type and categories of both aircraft.

Furthermore, according to the invention, it is expedient to calculate the actual distance between the aircraft on the basis of data on their velocity and positions in space.

Furthermore, according to the invention, it is expedient to analyze the hazard of wake turbulence based on the data concerning wake vortex circulations, distance between them and their location with respect to the intersection point of the sight line with the reference plane.

The specified task was also solved by the development of an on-board system ensuring minimum longitudinal separation distance under conditions of wake turbulence with at least one leading aircraft generating wake vortices and the second aircraft following the first one during takeoff or landing of said aircraft on the same runway or on two parallel runways located near each other, or during in-trail flight at neighboring altitudes when there is a risk of possible wake turbulence from the first aircraft along the course of the second aircraft, which includes a distance control device, a wake turbulence control device, a flight dynamics control device, and a visualization device that are connected to the aircraft electronic computing device, to the aircraft surveillance system, to the aircraft control system, and to the aircraft communication system, wherein:

the distance control device includes a data receiving unit, a data transmitting unit, a distance calculating unit, a reference plane simulating unit, and a distance comparing unit, and is intended for:
obtaining and storing information and building databases, which contain at least: data on the current movement parameters of the aircraft, in respect of which the provision of the minimum separation distance is assumed; data on the standardized minimum separation distance for the interaction of the aircraft in wake turbulence conditions; data describing the capabilities of the aircraft to change its velocity mode;
selecting the buffer zone value, providing the responsiveness of the pilot and the control system of the second aircraft to the command for changing its flight velocity, and for preserving the buffer zone value in the memory of the electronic device onboard the second aircraft;
estimating the recommended maximum distance value coinciding with the sight line and connecting gravity centers of the first and the second aircraft as the sum of the standardized minimum separation distance value and the buffer zone value, and storing the value of recommended maximum distance in the memory of the electronic device onboard the aircraft;
defining the reference distance value as the arithmetic average between the values of the specified standardized minimum separation distance and the recommended maximum distance;
simulating the reference plane on the edge of the buffer zone with the standardized minimum separation distance perpendicular to the sight line;
continuously calculating the current actual distance between the first and the second aircraft along the sight line and its continuous comparison with the value of recommended maximum distance, the value of reference distance, and the value of standardized minimum separation distance;
generating a report on exceedance, equality or reduction of the actual distance value in relation to the recommended maximum distance, the reference distance and the standardized minimum separation distance;
transmitting the generated report to the flight dynamics control device of the aircraft and to the communication system of the aircraft for further communication to the traffic control unit;

the wake turbulence control device includes a data receiving unit, a data transmitting unit, a unit for determination of the wake hazard level, and a unit for computing the risks of aircraft's interaction with the wake turbulence, and is intended for:
obtaining and storing information and building databases, which contain at least: data on the characteristic values of the wake vortex circulations of the first aircraft, on the distance between the circulations in the vicinity of the first aircraft, and on the change of this distance when progressively moving further away from the first aircraft; data on the acceptable risk thresholds of interaction of the second aircraft with dangerous wake turbulence;
receiving from the aircraft surveillance system of the airspace scan results obtained in the area of the specified reference plane on the edge of the buffer zone with the standardized minimum separation distance, that contain information on the parameters of the detected wake turbulence;
determination of the wake turbulence hazard level on the specified edge and risk assessment of the aircraft's interaction with dangerous wake turbulence by comparing the risk value to the admissible risk threshold;
generating a report on an inadmissible entrance area present on the edge of the buffer zone on the course of the second aircraft if the risk value exceeds the abovementioned threshold value, or generating a report on the absence of such an area;
continuous transmission of the generated report to the flight dynamics control device of the aircraft and to the communication system of the aircraft for their further communication to the traffic control unit;

the flight dynamics control device includes a data receiving unit, a data transmitting unit, a data complexification unit, and a unit for generating commands to the aircraft control system, and is intended for:
obtaining reports from the distance control device on the following events: the actual distance value exceeds the recommended maximum distance value; the actual distance is reduced the value smaller than the reference distance, but it exceeds the standardized minimum separation distance value; the actual distance value equals the recommended maximum distance; the actual distance value is reduced to the recommended maximum distance value and it exceeds the reference distance value;
obtaining the following reports from the turbulence control device: on an inadmissible area present on the edge of the buffer zone in case of the design risk value exceeding the threshold value; on the absence of an inadmissible area on the edge of the buffer zone if the design risk value is less than the threshold value;
generating a deceleration command incase an inadmissible area is detected on the edge of the buffer zone and the actual distance value is less than the value of the reference distance;
generating a deceleration command if an inadmissible area is absent on the edge of the buffer zone and the actual distance value is less than the value of the reference distance,
generating a deceleration command if an inadmissible area is absent on the edge of the buffer zone and the actual distance value is equal to the standardized minimum separation distance;

generating an acceleration command if an inadmissible area is absent on the edge of the buffer zone and the actual distance value is larger than the maximum reference distance;

generating an acceleration command if an inadmissible area is absent on the edge of the buffer zone and the actual distance value is larger than the maximum recommended distance;

transmitting the acceleration or deceleration command to the second aircraft control system;

the visualization device is adapted for dynamically generating and displaying on the screen of the second aircraft at least the following information: on the value of the actual distance, on the necessary transition to the deceleration mode, on receiving the deceleration command by the second aircraft control system, on the movement of the second aircraft in the deceleration mode, on the termination of the deceleration mode; on the necessity of transition to the acceleration mode, on receiving the acceleration command by the control system of the second aircraft, on the movement of the second aircraft in the acceleration mode, on the termination of the acceleration mode; on the constant velocity flight mode.

Furthermore, according to the invention, it is expedient that the visualization device shall be adapted to perform light indication of deceleration', acceleration and constant velocity modes with activation of indicators of different colors.

Furthermore, according to the invention, it is expedient that the visualization device shall be adapted to displaying the deceleration command receipt and acceleration command receipt with an intermittent light indication.

Furthermore, according to the invention, it is expedient that the distance control device shall be adapted to determine the standardized minimum separation distance based on the standards, set for the wake turbulence conditions at longitudinal separation taking into account the type and categories of both aircraft.

Furthermore, according to the invention, it is expedient that the distance control device shall be adapted to calculate the current actual distance between the aircraft based on the data concerning their velocity and location in space.

Furthermore, according to the invention, it is expedient that the wake turbulence control device shall be adapted to analyze the level of the wake turbulence hazard based on wake circulations, the distance between them and their location with respect to the point of intersection of the sight line with the reference plane.

LIST OF DRAWINGS

Figure 2:
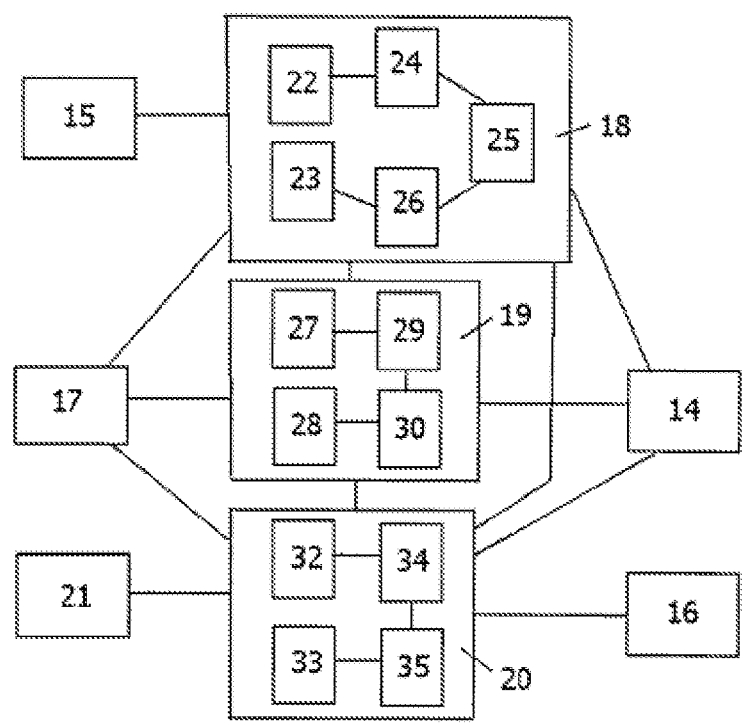

Hereinafter, the method for ensuring minimum longitudinal separation distance under wake vortex turbulence conditions and on-board system for its implementation according to the invention are illustrated by the examples of embodiment and the drawings attached, which demonstrate:

FIG. 1—a diagram illustrating relative position of the standardized minimum separation distance, buffer zone, reference distance and recommended maximum distance at implementation of the method according to the invention;

FIG. 2—a diagram of the on-board system according to the invention.

However, the implementation examples are not exhaustive, do not limit the possibilities of the invention embodiment and are not beyond the scope of the claims.

BEST EMBODIMENT OF THE INVENTION

The method for ensuring minimum longitudinal separation distance under wake turbulence conditions according to the invention can be implemented with the movement of at least one leading aircraft, generating wake vortices and the second aircraft following the first one during takeoff or landing on the same runway or on two parallel runways located near each other, or during in-trail flight at neighboring altitudes, when there is a risk of possible wake turbulence from the first aircraft along the course of the second aircraft, as illustrated in FIG. 1.

When moving along the course of the leading aircraft 1, generating a wake 2, and of the aircraft 3 following the aircraft 1 at the current actual distance 4, for example, during in-trail flight at neighboring altitudes, according to the invention, the compliance with the standardized minimum separation distance 5 shall be ensured, which is determined on the basis of the data on wake vortex turbulence conditions provided by the traffic control unit for longitudinal separation, taking into account the type and category of aircraft 1 and 3. According to the method for ensuring minimum longitudinal separation distance, the pilot of the aircraft 3 selects the value of the buffer zone 6, which provides the responsiveness of the pilot and the control system of the aircraft 3 to the command for changing its flight velocity. At the same time, the value of the buffer distance 6 can be selected based on the skills of the pilot and velocity control system of the aircraft 3; it may be changed during the flight as the flight performances of the aircraft are changed; it may be different for different types of aircraft.

According to the invention, along the sight line 7 connecting the gravity centers of the aircraft 1 and 3, it is possible to define the design value of the recommended maximum distance 8 as the sums of the value of the specified minimum separation distance 5 and the value of the buffer zone 6.

It is known that the intensity of acceleration and deceleration of the aircraft in nearly horizontal flight depends on the excess thrust, and aircraft acceleration performances depend, to a large extent, on the engine acceleration capability—the time interval from the beginning of throttle advancing to the achievement of the specified increased thrust mode. It is also known that for the in-flight deceleration of the aircraft, the engines are switched to the flight idling power mode, and to increase the drag, brake flaps, gear extension, and other means may be applied. Due to the fact that according to this method, control over the execution of the aircraft braking and acceleration mode is granted to the pilot, he can execute the deceleration or acceleration command and maintain the deceleration or acceleration mode by using standard techniques of deceleration or acceleration or maintain the current mode unchanged if the command to change the mode has not been received.

According to the invention, the value of the reference distance 9 is defined as the arithmetic average between the values of the specified standardized minimum separation distance 5 and the recommended maximum distance 8.

According to the invention, a simulation of the reference plane 10 on the edge 11 of the buffer zone 6 with the limit of the standardized minimum separation distance 5 is performed. The reference plane 10 is used to determine the presence or absence of wake turbulence at the edge 11 of the buffer zone 6 according to the airspace observation results made by the aircraft surveillance system, and to assess their hazard level for the aircraft 3, for example, based on the data that characterize in the reference plane 10 wake vortex circulations 12, distance between circulations 12, and location of circulations 12 with respect to the intersection point 13 of the sight line 7 with the reference plane 10.

On-board system for ensuring minimum longitudinal separation distance under wake turbulence conditions, according to the invention and in the variant presented in FIG. 2, includes the distance control device 18, the wake turbulence control device 19, the flight dynamics control device 20, and the renderer 21 that are connected at least to the aircraft electronic computing device 14, to the aircraft surveillance system 15, to the aircraft control system 16, and to the aircraft communication system 17.

The distance control device 18 includes the data receiving unit 22, the data transmitting unit 23, the distance calculating unit 24, the reference plane simulating unit 25, and the distance comparing unit 26, and ensures:
- obtaining and storing of information and building databases;
- determining the standardized minimum separation distance 5;
- selecting the buffer zone 6 value in the dynamic mode and saving the selected value;
- calculating the recommended maximum distance 8 value and preserving the calculated values;
- calculating the reference distance 9 value as the average between the values of recommended maximum distance 8 and standardized minimum separation distance 5;
- simulating the reference plane 10 on the edge 11 of the buffer zone 6 with the standardized minimum separation distance 5 perpendicular to the sight line 7;
- continuously calculating the current actual distance 4 and its continuous comparison with the recommended maximum distance 8 value, reference distance 9 value, and standardized minimum separation distance 5 value;
- generating a report on exceeding or reducing the actual distance 4 in relation to the recommended maximum distance 8, reference distance 9 and minimum separation distance 5, or reports on the equality of the actual distance 4 to one of the specified values;
- transmitting the generated report to the flight dynamics control device 20 of the aircraft 3, to the aircraft electronic computing device 14 and to the aircraft communication system 17 for their communication to the traffic control unit.

Furthermore, according to the invention, the distance control device 18 can be adapted to determine the standardized minimum separation distance 5 based on the standards set for wake turbulence conditions for longitudinal separation taking into account the type and category of the aircraft 1 and 3.

Furthermore, the distance control device 18 can be adapted to calculate the actual distance 4 based on the velocity of the aircraft 1 and 3 and their location in space.

Furthermore, the data receiving unit 22, data transmitting unit 23, distance calculating unit 24, reference plane simulating unit 25, and distance comparing unit 26 can be realized by using the existing on-board aircraft equipment and implementing various acceptable computing algorithms.

The wake turbulence control device 19 contains the data receiving unit 27, the data transmitting unit 28, the unit for determination of the wake hazard level 29, and the unit for computing the risks of aircraft's interaction with wake turbulence 30, and ensures:
- obtaining and storing information and construction of databases;
- receiving from the aircraft surveillance system 15 the results of the airspace scan obtained in the area of the specified reference plane 10 on the edge 11 of the buffer zone 6 with the standardized minimum separation distance 5;
- generating a report on an inadmissible entrance area 31 (FIG. 1) present on the edge 11 of the buffer zone 6 at the direction of the aircraft 3 movement if the risk value exceeds the abovementioned threshold value, or generating a report on the absence of such an area;
- determining the hazard level of the wake vortex 2 turbulence on the edge 11 and assessing the risk of aircraft 3 interacting with the dangerous wake turbulence in an inadmissible area 31 by comparing the risk value to the admissible risk threshold;
- continuously transmitting the generated report to the aircraft electronic computing device 14, to the flight dynamics control device of the aircraft 20 and to the communication system of the aircraft 3 for their further communication to the traffic control unit.

Furthermore, according to the invention, the wake turbulence control device 19 can be adapted for analysis of the wake turbulence hazard level based on its circulations 12, distance between circulations 12, and location of circulations 12 with respect to the point of intersection 13 of the sight line 7 with the reference plane 10.

The data receiving unit 22, data transmitting unit 23, distance calculating unit 24, reference plane simulating unit 25, and distance comparing unit 26 can be realized by using the existing on-board equipment and implementing different methods of analyzing wake turbulence hazard level.

The flight dynamics control device 20 includes the data receiving unit 32, the data transmitting unit 33, the data complexification unit 34, and the unit 35 for generating commands to the aircraft control system, and ensures:
- obtaining reports from the distance control device 18 concerning the following events: the value of the actual distance 4 exceeds the value of the recommended maximum distance 8; the value of the actual distance 4 equals the recommended maximum distance 8; the actual distance 4 value equals or exceeds the maximum reference distance 9; the value of the actual distance 4 is less than the value of the reference distance 9; the value of the actual distance 4 equals the standardized minimum separation distance 5;
- obtaining reports from the turbulence control device 19 on the absence or presence of the inadmissible area 31 on the edge 11 of the buffer zone 6;
- generating a deceleration command if the inadmissible area 31 is present on the edge 11 of the buffer zone 6, and if the actual distance 4 is less than the reference distance 9 value;
- generating a deceleration command if the inadmissible area 31 is absent on the edge 11 of the buffer zone 6, and if the actual distance 4 is less than the value of the reference distance 9;
- generating a deceleration command if the inadmissible area 31 is absent on the edge 11 of the buffer zone 6, and if the actual distance 4 is equal to the standardized minimum separation distance 5;
- generating an acceleration command if an inadmissible area 31 is absent on the edge 11 of the buffer zone 6, and if the actual distance is larger than the maximum reference distance 9;
- generating an acceleration command if an inadmissible area 31 is absent on the edge 11 of the buffer zone 6, and if the actual distance 4 is larger than the recommended maximum distance 8;

transmitting the acceleration or deceleration command to the aircraft 3 control system 16.

The visualization device 21 ensures dynamically generating and displaying on the screen of the aircraft 3 information at least on the value of the actual distance 4, on the necessary transition into the braking mode, on receiving the braking command by the control system 16 of the aircraft 3, on the movement of the aircraft 3 in the deceleration mode, on the termination of the deceleration mode; on the necessity of transition to the acceleration mode, on receiving the acceleration command by the aircraft 3 control system 16, on the movement of the aircraft 3 in the acceleration mode, on the termination of the acceleration mode; on the constant velocity flight mode.

The visualization device 21, according to the invention, can be adapted to perform light indication of deceleration, acceleration, and constant velocity modes, with activation of indicators of different colors and configurations, for example, according to the traffic light type: red light—deceleration, green light—constant velocity mode, blue light—acceleration mode. This indication can be performed in different modes of interruption while indicating the necessity to transit to another flight mode and indicating deceleration or acceleration command receipt by the control system 16 of the aircraft 3 and in continuous mode, during the aircraft's movement in the deceleration or acceleration mode, respectively.

These specified distance control device 18, wake turbulence control device 19, flight dynamics control device 20, visualization device 21, and their integrated units can be realized with adaptation of the existing on-board aircraft equipment to the fulfillment of new tasks using appropriate computational algorithms and software.

The method for ensuring minimum longitudinal separation distance under wake turbulence conditions, according to the invention, is implemented by using the selected standardized minimum separation distances, the calculated values of the recommended maximum distance 8, reference distance 9, and buffer zone 6, and database information generated by the distance control device 18 and containing, data at least on: the current movement parameters of the aircraft, in respect of which the provision of the minimum separation distance is assumed; the standardized minimum separation distance for the interaction of the aircraft in wake turbulence; the capacities of the aircraft to change the velocity modes; as well as database information generated by the wake turbulence control device 19 and containing, data at least on: the characteristic values of the wake 2 circulations 12 of the aircraft 1, on the distance between the circulations 12 in the vicinity of the aircraft 1, and on the change of this distance as the wake 2 progressively moves away from the aircraft 1; data on the acceptable risk thresholds of the interaction of the aircraft 3 with the dangerous wake turbulence.

To implement the method in accordance with the invention, it is required to carry out, with the help of the distance control device 18, a continuous calculation of the current actual distance 4 between the aircraft 1 and, to perform its continuous comparison with the recommended maximum distance 8 value, the reference distance 9 value, and the standardized minimum separation distance 5 value, stored in the database of the distance control device 18. Using the distance control device 18, it is possible to generate a report on exceedance, equality or reduction of the actual distance 4 in relation to the recommended maximum distance 9 and to the minimum separation distance 5; or a report on the equality of the actual distance 4 to one of these values. The generated reports are transmitted to the flight dynamics control device 20 and to the aircraft communication system 17 for their further communication to the traffic control unit. The calculations, specified in this method, can be performed using electronic means and known calculation algorithms.

The wake turbulence control device 19 communicates directly with the aircraft 3 surveillance system 15 and receives the results of the airspace scan, obtained in the area of the specified reference plane 10 at the edge 11 of the buffer zone 6 with the standardized minimum separation distance 5, that contain information on the parameters of the detected wake turbulence; determines the wake hazard level on the edge 11; assesses the risk of the interaction of plane 3 with the dangerous turbulence from the wake 2 by comparing the risk assessment to the acceptable risk threshold. In case the risk value exceeds the abovementioned threshold value, the wake turbulence control device 19 generates a report on the presence of an inadmissible entrance area 31 on the edge 11 of the buffer zone 6 on the course of the aircraft 3 and, if the risk value is less than the threshold value, a report on the absence of the inadmissible area is generated. The wake turbulence control device 19 continuously transmits the generated reports to the flight dynamics control device 20 and to the aircraft 3 communication system 17 for their further communication to the traffic control unit.

The flight dynamics control device 20, based on the report from the distance control device 18 on the exceedance, equality or reduction of the actual distance 4 in relation to the recommended maximum distance 8 value, the reference distance 9 value, and the standardized minimum separation distance 5 value, as well as based on the reports received from wake turbulence control device 19 on the presence or absence on the edge 11 of the buffer zone 6 of an area 31, inadmissible for the entrance of aircraft 3, generates a deceleration or acceleration command or generates a report on the absence of such a necessity.

If the report on the presence of an inadmissible area 31 on the edge 11 of the buffer zone 6 is urgent, and if the value of the actual distance 4 is less than the value of the reference distance 9, a deceleration command is generated, which increases the actual distance 4 up to the value of reference distance 9 and, therefore, increases the distance between the aircraft 3 and the edge 11 of the standardized minimum separation distance 5.

If both reports on the presence of an inadmissible area 31 on the edge 11 of the buffer zone 6 and on the value of the actual distance 4 being less than the value of the reference distance 9 turn out to be simultaneously urgent, a deceleration command is generated, which increases the actual distance 4, for example, up to the value of the reference distance 9.

If both reports on the presence of an inadmissible area 31 on the edge 11 of the buffer zone 6 and on the value of the actual distance 4 being equal to the standardized minimum separation distance 5 turn out to be simultaneously urgent, a deceleration command is generated, which ensures an increase of the actual distance 4, for example, up to the value of the reference distance 9.

If both reports on the absence of an inadmissible area 31 and on the value of the actual distance 4 being larger than the value of the maximum reference distance 9, but less than the recommended maximum distance 8, turn out to be simultaneously urgent, an accelerating command is generated, which reduces the actual distance 4 down to the value of the reference distance 9.

If both reports on the absence of an inadmissible area 31 and on the value of the actual distance 4 being larger than the value of the recommended maximum distance 8 turn out to be simultaneously urgent, an accelerating command is generated, which reduces the actual distance 4 down to the value of reference distance 9.

During the deceleration or acceleration mode of the aircraft 3, the real situation will be altered, and, at receiving of other reports, the flight dynamics control device 20 will generate another command or stay in the previous mode depending on whether the change of the aircraft velocity takes place to change the actual distance 4 between the aircraft.

It should be clear to the air traffic specialists that, according to the invention, the present method not only ensures the protection of the following aircraft 3 from the hazard of the wake 2 behind the leading aircraft 1 and the maintenance of the standardized minimum separation distance 5, but also compensates the non-observance of the distances between the aircraft caused by deceleration or acceleration of the leading aircraft 1.

Information on the actual flight situation and its changes, which led to the need for a prompt response, is displayed by the renderer 21 on the screen of the aircraft 3 and may contain information on the actual distance value; on velocity changes; on the receipt of a deceleration command by the control system 16 of the aircraft 3; on movement of the aircraft 3 in the deceleration mode; on the termination of the deceleration mode; on the receipt of an acceleration command by the control system 16 of the aircraft 3; on the movement of the aircraft 3 in the acceleration mode; on the termination of the acceleration mode; on the constant velocity flight mode.

The visualization device 21 can provide a symbolic and/or light indication, for example, with activation of indicators of different colors and configurations according to the traffic light type: red light—deceleration, green light—constant velocity mode, blue light—acceleration mode. This indication can be, for example, intermittent, with different intervals of signal interruption, when informing about the necessity to change the velocity and receiving a command by the aircraft control system 16; and continuous, when the aircraft moves in the deceleration or acceleration mode, respectively.

It should be clear to the air traffic specialists that the information coming from the on-board system may be used to generate the black box reference data that, in the event of dangerous collision, will allow to analyze the compliance with the longitudinal separation and pilot's behavior regardless of the actions of the ATC officer.

The method and on-board system for ensuring minimum longitudinal separation distance under wake turbulence conditions according to the invention have obvious advantages in comparison with the known proposed and currently implemented technical solutions, as they both ensure compliance with the standardized minimum separation distance and offer the means of its maintenance within the set limits without compromising wake vortex safety, which allows to improve the flight dispatching process and increase the airport capacity, as well as to avoid the impact of the "human factor" conditioned by the experience of the pilot and flying control officer and by their ability to make quick decisions on the flight operation process in dangerous situations.

Industrial applicability Method and on-board system for ensuring minimum longitudinal separation distance under wake turbulence conditions according to the invention can be implemented using the known technologies and equipment and can find their application for aircraft of any category and destination, which will help to increase the airport capacity and reduce the probability of flight accidents.

The invention claimed is:

1. A method for ensuring minimum longitudinal separation distance under wake turbulence conditions with at least one leading aircraft generating wake vortices and a second aircraft following the first aircraft during at least one of takeoff or landing on the same runway, takeoff or landing on two parallel runways located near each other, or in-trail flight at neighboring altitudes when there is a risk of possible wake turbulence from the first aircraft along the course of the second aircraft, the method comprising:

selecting a value of a buffer zone (6) which provides a possibility for a pilot and a control system of the second aircraft to respond to a command for changing a flight speed of the second aircraft;

determining a value of the recommended maximum distance (8) between the first aircraft and the second aircraft as a sum of a value of a standardized minimum separation distance (5) for the interaction of the first aircraft and the second aircraft under wake turbulence conditions and a value of the buffer zone (6), the recommended maximum distance (8) defined as a distance along the sight line (7) of the connecting gravity centers of the first aircraft and the second aircraft;

a value of the reference distance (9) as an arithmetic average of the values of said standardized minimum separation distance (5) and the value of the recommended maximum distance (8), for monitoring of deviation of the recommended maximum distance (9) from a current actual distance (4);

continuously determining a value of the current actual distance (4) between the first aircraft and the second aircraft, and comparing the current actual distance (4) with the values of the recommended maximum distance (8), the reference distance (9) and continuously comparing the standardized minimum separation distance (5) for detection of the distance exceeding, equaling or decreasing below the actual distance (4) in comparison with the abovementioned values;

continuously monitoring air space along the course of the second aircraft in a simulated reference plane (10) on the edge (11) of the buffer zone (6) at the standardized minimum separation distance (5) to determine a presence or absence of the wake turbulence in the said reference plane (10) and the level of the wake hazard for the second aircraft;

when detecting danger wake turbulence in the reference plane (10), assessing the risk of the second aircraft interaction with the said turbulence and, if the risk exceeds a predetermined admissible threshold, defining the turbulence location as an inadmissible area (31) for entrance of the second aircraft;

upon detection of the inadmissible area (31) on the edge (11) of the buffer zone (6) with the actual distance (4) less than the reference distance (9) value, generating a deceleration command;

in the absence of the inadmissible area (31) at the edge (11) of the buffer zone (6) and the value of the actual distance (4) less than the value of the reference distance (9), generating a deceleration command;

in the absence of the inadmissible area (31) at the edge (11) of the buffer zone (6) and the value of the actual distance (4) equal to the standardized minimum separation distance (5), generating a deceleration command;

in the absence of the inadmissible area (31) at the edge (11) of the buffer zone (6) and the value of the actual distance (4) larger than the value of the reference distance (9), generating an acceleration command;

in the absence of the inadmissible area (31) at the edge (11) of the buffer zone (6) and the value of the actual distance (4) larger than the recommended maximum distance (8), generating an acceleration command;

using the traffic control unit to dynamically store and transmit information:

on relative positions of the second aircraft and the first aircraft along the course of the second aircraft;

on the value of the selected buffer zone (6);

on the value of the calculated recommended maximum distance (8);

on the value of the calculated reference distance (9);

on the value of the actual distance (4) between the first aircraft and the second aircraft;

on a determined necessity of switching to the deceleration mode, on the receipt of the deceleration command by the control system of the second aircraft, on the movement of the second aircraft in the deceleration mode, on the termination of the deceleration mode; and on a determined necessity of switching to the acceleration mode, on the receipt of the acceleration command by the control system of the second aircraft, on the movement of the second aircraft in the acceleration mode, on the termination of the acceleration mode;

dynamically displaying, on a screen of the second aircraft, information at least on the value of the actual distance between the first aircraft and the second aircraft and, at least with help of light indication, information on the determined necessity of switching to the deceleration mode, information on the receipt of the deceleration command, information on the execution of the deceleration mode, information on the termination of the deceleration mode, information on the determined necessity of switching to the acceleration mode, information on the receipt of the acceleration command by the control system of the second aircraft, information on the execution of the acceleration mode, and information on the termination of the acceleration mode; and providing, to the pilot of the second aircraft, during the time of the light indication, a possibility to execute the deceleration mode or the acceleration mode using standard techniques of deceleration or acceleration, or to maintain the current mode without changes.

2. The method according to claim 1, in which the light indication of the determined necessity to change the speed and of the receipt of the acceleration command is displayed through an intermittent light indication.

3. The method according to claim 1, in which the light indication of the deceleration mode, acceleration mode, and constant speed mode is performed through activation of indicators of different colors.

4. The method according to claim 1, in which the standardized minimum separation distance (5) is determined on the basis of standards set for wake turbulence conditions for longitudinal separation, taking into account the type and categories of the first and the second aircraft.

5. The method according to claim 1, in which the current actual distance between the aircraft is calculated, based on their speed and location in space.

6. The method according to claim 1, in which the wake turbulence hazard level is analyzed based on wake circulations, distance between them, and their location with regard to the point of intersection of the sight line with the reference plane.

7. An on-board system for ensuring minimum longitudinal separation distance under wake turbulence conditions with at least one leading aircraft generating the wake cortices and a second aircraft following the first aircraft during takeoff or landing on the same runway or on two parallel runways located near each other, or during the in-trail flight at neighboring altitudes when there is a risk of possible wake turbulence from the first aircraft along the course of the second aircraft, the on-board system comprising a distance control device (18), a wake vortex (2) turbulence control device (19), a flight dynamics control device (20), and a renderer (21), each connected with an aircraft electronic computing device (14), an aircraft surveillance system (15), an aircraft control system (16), and aircraft communication system (17), wherein:

the distance control device (18) includes a data receiving unit (22), a data transmitting unit (23), a distance calculating unit (24), a reference plane (10) simulating unit (25), and a distance comparing unit (26) and configured to:

obtain and store the information and constructing databases containing data at least on: current movement parameters of the aircraft, in respect to an estimated minimum separation distance; standardized minimum separation distance for interaction of the aircraft under wake turbulence conditions; capabilities of the second aircraft to change its speed mode;

select a buffer zone (6) value which provides a possibility for the pilot and a control system of the second aircraft to respond to a command for changing the flight speed, and to preserve a value of the buffer zone in the memory of the on-board electronic device of the second aircraft;

estimate a recommended maximum distance (8) value, coinciding with the sight line (7) and connect gravity centers of the first aircraft and the second aircraft, as a sum of a value of the standardized minimum separation distance (5) and a buffer zone (6) value, and preserve the recommended maximum distance (8) value in the memory of the on-board electronic device of the second aircraft;

define a reference distance (9) value as an arithmetic average of the values of the standardized separation minimum distance (5) and the recommended maximum distance (8);

simulate a reference plane (10) at an edge (11) of the buffer zone (6) with the standardized minimum separation distance (5) perpendicular to the sight line (7);

continuously calculate a current actual distance (4) between the first aircraft and the second aircraft along the sight line (7) and continuously compare the current actual distance (4) with the values of the recommended maximum distance (8), the reference distance (9), and the standardized minimum separation distance (5);

generate a report on the distance exceeding, equaling or decreasing below the actual distance (4) value as compared to the recommended maximum distance (8), the reference distance (9) and the standardized minimum separation distance (5);

transmit the generated reports to the flight dynamics control device (20) of the aircraft and to the aircraft communication system (17) for further communication to a traffic control unit;

the wake turbulence control device (19) comprising a data receiving unit (27), a data transmitting unit (28), a unit (29) for determination of the wake hazard level, and a unit (30) for computing a risk of interaction of the aircraft with the wake turbulence, and configured to:

obtain and store the information and building databases, containing data at least on: characteristic values of circulations (12) of the wake vortices (2) from the first aircraft, a distance between the circulations (12) in the vicinity of the first aircraft, and change of this distance when progressively moving further away from the first aircraft; on admissible risk thresholds of interaction of the second aircraft with dangerous wake turbulence;

receive from the aircraft surveillance system (15) the results of airspace scanning in the area of the specified reference plane (10) on the edge (11) of the buffer zone (6) with the standardized minimum separation distance (5), that contain information on parameters of the detected wake turbulence;

determine a wake turbulence hazard level on the edge (11) and assess the risks of interaction of the aircraft with wake dangerous turbulence by comparing the risk with the admissible risk;

generate a report on an inadmissible entrance area (31) at the edge (11) of the buffer zone (6) in the direction of the second aircraft movement if the risk value exceeds the admissible risk threshold, or generate a report on the absence of the inadmissible area (31);

continuously transmit the generated report to the flight dynamics control device (20) and to the aircraft communication system (17) for further communication to the traffic control unit;

the flight dynamics control device (20) comprising a data receiving unit (32), a data transmitting unit (33), a data processing unit (34), and a unit (25) for generating commands to the aircraft control system (16), and is configured to:

receive reports from the distance control device (18) on: the value of the recommended maximum distance (8) exceeding the value of the actual distance (4); the actual distance (4) reduced down to a value lower than the reference distance (9) but above the value of standardized minimum separation distance (5); the value of the actual distance (4) equaling the value of the recommended maximum distance (8); the value of the actual distance (4) equaling the value of standardized minimum separation distance (5); the actual distance (4) reduced down to a value lower than the value of the recommended maximum distance (8) but above the value of the reference distance (9);

receive reports from the turbulence control device (19): on the presence of the inadmissible area (31) at the edge (11) of the buffer zone (6) if the computed risk value exceeds the admissible risk threshold; and on absence of the inadmissible area (31) at the edge of the buffer zone (6) if the computed risk value is less than the admissible risk threshold;

upon detection of the inadmissible area (31) at the edge (11) of the buffer zone (6) and the value of the actual distance (4) less than the value of the reference distance (9), generate a braking command;

in the absence of the inadmissible area (31) at the edge (11) of the buffer zone (6) and the value of the actual distance (4) is less than the value of the reference distance (9), generate a braking command;

in the absence of the inadmissible area (31) at the edge (11) of the buffer zone (6) and the value of the actual distance (4) is equal to the standardized minimum separation distance (5), generate a braking: command;

in the absence of the inadmissible area (31) is absent at the edge (11) of the buffer zone (6) and the value of the actual distance (4) is larger than the maximum reference distance (9), generate an acceleration command;

in the absence of the inadmissible area (31) is absent at the edge (11) of the buffer zone (6) and the value of the actual distance (4) is larger than the maximum recommended distance (8), generate an acceleration command;

transmitting an acceleration command or braking command to the control system (16) of the second aircraft;

a visualization device configured to dynamically generate and display on a screen of the second aircraft information at least on: a value of the actual distance, a determined necessity of switching to the deceleration mode, receipt of the deceleration command by the control system of the second aircraft, movement of the second aircraft in the deceleration mode, termination of the deceleration mode; a determined necessity of switching to the acceleration mode, receiving the acceleration command by the control system of the second aircraft, movement of the second aircraft in the acceleration mode, termination of the acceleration mode; information on the constant speed flight mode.

8. The system according to claim 7, in which the visualization device (21) is adapted for performing light indication of the braking, acceleration and constant speed modes with activation of indicators of different colors.

9. The system according to claim 7, in which the visualization device (21) is adapted for displaying the information on the determined necessity of changing the speed and on the receipt of the braking or acceleration commands with an intermittent light indication.

10. The system according to claim 7, in which the distance control device (20) is adapted for determination of the standardized minimum separation distance (5) on the basis of standards for the wake turbulence conditions for longitudinal separation, taking into account the type and categories of the first aircraft and the second aircraft.

11. The system according to claim 7, in which the distance control device (20) is adapted for calculation of the current actual distance (4) between the aircraft, based on the data on their speed and location in space.

12. The system according to claim 7, in which the wake turbulence control device (19) is adapted for analysis of the wake turbulence risk, based on the data on the wake circulations (12), a distance between the circulations (12) and location of the circulations (12) with respect to the intersection point (13) of the sight line (7) with the reference plane (19).

* * * * *

UNITED STATES PATENT AND TRADEMARK OFFICE
CERTIFICATE OF CORRECTION

PATENT NO.       : 9,466,220 B2
APPLICATION NO.  : 14/421586
DATED            : October 11, 2016
INVENTOR(S)      : Sergey Viktorovich Alekseev et al.

It is certified that error appears in the above-identified patent and that said Letters Patent is hereby corrected as shown below:

In the Claims

Claim 1, Column 14, Line 28, before "a value" please insert --determining--.

Signed and Sealed this
Sixth Day of December, 2016

Michelle K. Lee
*Director of the United States Patent and Trademark Office*